US012662425B2

(12) United States Patent
Kim et al.

(10) Patent No.: US 12,662,425 B2
(45) Date of Patent: Jun. 23, 2026

(54) MARINE CONCRETE COMPOSITION USING DECHLORINATION MICROORGANISM, AND CONSTRUCTION METHOD OF MARINE CONCRETE STRUCTURE FOR THE SAME

(71) Applicants: KOREA INSTITUTE OF CIVIL ENGINEERING AND BUILDING TECHNOLOGY, Gyeonggi-do (KR); Four-m Co., Ltd., Gwangju (KR)

(72) Inventors: Kyong-Chul Kim, Seoul (KR); Kwang-Mo Lim, Gyeonggi-do (KR); Kyung-Taek Koh, Gyeonggi-do (KR); Gum-Sung Ryu, Gyeonggi-do (KR); Sung Yong Park, Gyeonggi-do (KR); Jae-Yoon Kang, Gyeonggi-do (KR); Gi-Hong An, Gyeonggi-do (KR); Kihyon Kwon, Gyeonggi-do (KR); Nam-Kon Lee, Gyeonggi-do (KR); Soonku Yoon, Gwangju (KR); Jueng wan Go, Gwangju (KR); Dong ha Lee, Gwangju (KR)

(73) Assignees: KOREA INSTITUTE OF CIVIL ENGINEERING AND BUILDING TECHNOLOGY, Gyeonggi-do (KR); Four-m Co., Ltd., Gwangju (KR)

( * ) Notice: Subject to any disclaimer, the term of this patent is extended or adjusted under 35 U.S.C. 154(b) by 312 days.

(21) Appl. No.: 18/503,128

(22) Filed: Nov. 6, 2023

(65) Prior Publication Data

US 2024/0270646 A1 Aug. 15, 2024

(30) Foreign Application Priority Data

Nov. 16, 2022 (KR) ......................... 10-2022-0153308

(51) Int. Cl.
*C04B 24/00* (2006.01)
*C04B 14/48* (2006.01)
(Continued)

(52) U.S. Cl.
CPC .............. *C04B 24/00* (2013.01); *C04B 14/48* (2013.01); *C04B 18/146* (2013.01);
(Continued)

(58) Field of Classification Search
CPC ....... C04B 24/00; C04B 14/48; C04B 18/146; C04B 40/0675; C04B 2103/0001;
(Continued)

(56) References Cited

U.S. PATENT DOCUMENTS 9,926,234 B2 * 3/2018 Toussaint ................ C04B 14/28
2008/0261027 A1 * 10/2008 Li ........................... C04B 28/04
106/713

(Continued)

FOREIGN PATENT DOCUMENTS

CA 2670049 C * 10/2011
WO WO-2009146436 A1 * 12/2009 ............. C04B 18/02

OTHER PUBLICATIONS

Improvement of Biomineralization of Sporoscarcina pasteurii as Biocementing Material for concrete repair by atmospheric and room temperature plasma mutagensis and response to surface methodology P Han W Geng M Li S Jia J Yin R Xue J Microbiol. Biotechnol 2021 31(9) 13-11-1322 (Year: 2021).*

(Continued)

*Primary Examiner* — Pamela H Weiss
(74) *Attorney, Agent, or Firm* — JCIPRNET

(57) ABSTRACT

Provided are a marine concrete composition using dechlorination microorganisms capable of easily removing chlorine generated by seawater through an electrical method by allowing electrons emitted from electricity-generating
(Continued)

microorganisms to flow through steel fibers incorporated into ultra-high-performance concrete (UHPC) or high-performance fiber reinforced concrete (HPFRCC) through a dechlorination microbial capsule carrier and capable of self-healing concrete crack sites through a self-healing microbial capsule carrier and is also capable of fundamentally solving the problem of reduced durability against salt damage of ultra-high-performance concrete or high-performance fiber reinforced concrete for application in marine construction environments through a dechlorination microbial capsule carrier, and a method for constructing a marine concrete structure using the same.

10 Claims, 12 Drawing Sheets

(51) Int. Cl.

| | |
|---|---|
| *C04B 18/14* | (2006.01) |
| *C04B 40/06* | (2006.01) |
| *C04B 103/00* | (2006.01) |
| *C04B 103/30* | (2006.01) |
| *C04B 103/56* | (2006.01) |
| *C04B 111/20* | (2006.01) |
| *C04B 111/24* | (2006.01) |
| *C12N 1/20* | (2026.01) |
| *C12N 11/14* | (2006.01) |

(52) U.S. Cl.
CPC ............ *C04B 40/0675* (2013.01); *C12N 1/20* (2013.01); *C12N 11/14* (2013.01); *C04B 2103/0001* (2013.01); *C04B 2103/302* (2013.01); *C04B 2103/58* (2013.01); *C04B 2111/2038* (2013.01); *C04B 2111/24* (2013.01)

(58) Field of Classification Search
CPC .......... C04B 2103/302; C04B 2103/58; C04B 2111/2038; C04B 2111/24; C04B 28/10; C04B 2111/00068; C04B 2111/74; C04B 2201/52; C04B 28/02; C04B 7/24; C12N 1/20; C12N 11/14; C12N 11/04; E02B 17/0008
See application file for complete search history.

(56) References Cited

U.S. PATENT DOCUMENTS

| | | | | |
|---|---|---|---|---|
| 2011/0067605 A1* | 3/2011 | Constantz | ............... | C04B 28/02 |
| | | | | 106/739 |
| 2012/0031303 A1* | 2/2012 | Constantz | ............... | C04B 14/26 |
| | | | | 106/640 |

OTHER PUBLICATIONS

Production of ultra high performance concrete with Low energy consumption and Carbon Footprint using Supplementary Cementitious materials instead fo Silica Fume a Review M Hamad, M Nasr A shubbar Z Al Khafaji Z Al Masoodi O Al-Hashimi P Kot R Alkhaddar and K hashim Energies 2021 14 8291 (26 pps) (Year: 2021).*

Recent Advances in Microbial Viability Self healing preformance in bacterial based cement materials Kim Son Seo Lee Construction and Building materials 274 (2021) 122094 (Year: 2021).*

State of the Art Review of Microbial Induced Calcite Precipitation and Its Sustainability in Engineering Applications M Rahman R Hora I Ahenkorah S Beecham M Karim A Iqbal Sustainability 2020 12 6281 (Year: 2020).*

* cited by examiner

Bacteria

Oxygen

Water

Precipitated
Minerals a)

b)

c)

| Classification | | Ultra-high performance concrete(UHPC) | | Remarks |
|---|---|---|---|---|
| | | Composition ratio (parts by weight) | Optimal blending ratio | |
| Binder (B) | Cement | 100 parts by weight | 100 parts by weight | |
| | Silica fume | 10 ~ 30 parts by weight | 25 parts by weight | |
| Fine aggregate | | 100 ~ 140 parts by weight | 110 parts by weight | - Quartz sand with particle diameter of 0.5 mm or less |
| Filler | | 15 ~ 30 parts by weight | 25 parts by weight | - Quartz powder<br>- Average particle diameter 4μm |
| Mixing water (W) | | 15 ~ 25 parts by weight | 18 parts by weight | - W/B (ratio of water and binder) is 0.2 or less |
| Expansion material | | 1 ~ 3 parts by weight | 2 parts by weight | |
| Shrinkage reducing agent | | 1 ~ 3 parts by weight | 2 parts by weight | |
| Water reducing agent | | 4 ~ 7 parts by weight | 5 parts by weight | - Polycarboxylic acid-based |
| Self-healing microbial capsule | | · Incorporation of 0.5 to 2% based on total volume of ultra-high performance concrete (optimally 1 to 1.5% incorporation)<br>· 1μm ~ 400μm | | |
| Dechlorination microbial capsule | | · Incorporation of 1 to 5% based on total volume of ultra-high performance concrete (optimally 2.5 to 3.5% incorporation)<br>· 50μm ~ 400μm | | |
| Steel fiber | | · Incorporation of 1.5 to 3% based on total volume of ultra-high performance concrete (optimally 2 to 2.5% incorporation)<br>· Electrically conductive | | |

FIG. 10

| Classification | | Ultra-high performance concrete(UHPC) | | Remarks |
|---|---|---|---|---|
| | | Composition ratio (parts by weight) | Optimal blending ratio | |
| Binder (B) | Cement | 100 parts by weight | 100 parts by weight | |
| | Silica fume | 10 ~ 30 parts by weight | 25 parts by weight | |
| Fine aggregate | | 100 ~ 140 parts by weight | 110 parts by weight | - Quartz sand with particle diameter of 0.5 mm or less |
| Filler | | 15 ~ 30 parts by weight | 25 parts by weight | - Quartz powder<br>- Average particle diameter 4μm |
| Mixing water (W) | | 22 ~ 64 parts by weight | 30 parts by weight | - W/B (ratio of water and binder) is 0.2 to 0.4 |
| Expansion material | | 1 ~ 3 parts by weight | 2 parts by weight | |
| Shrinkage reducing agent | | 1 ~ 3 parts by weight | 2 parts by weight | |
| Water reducing agent | | 10 ~ 30 parts by weight | 20 parts by weight | - Polycarboxylic acid-based |
| Self-healing microbial capsule | | - Incorporation of 0.5 to 2% based on total volume of cementitious composite (optimally 1 to 1.5% incorporation)<br>- 1μm ~ 400μm | | |
| Dechlorination microbial capsule | | - Incorporation of 1 to 5% based on total volume of cementitious composite (optimally 2.5 to 3.5% incorporation)<br>- 300μm ~ 400μm | | |
| Steel fiber | | - Incorporation of 1.5 to 3% based on total volume of cementitious composite (optimally 2 to 2.5% incorporation)<br>- Electrically conductive | | |

FIG. 11

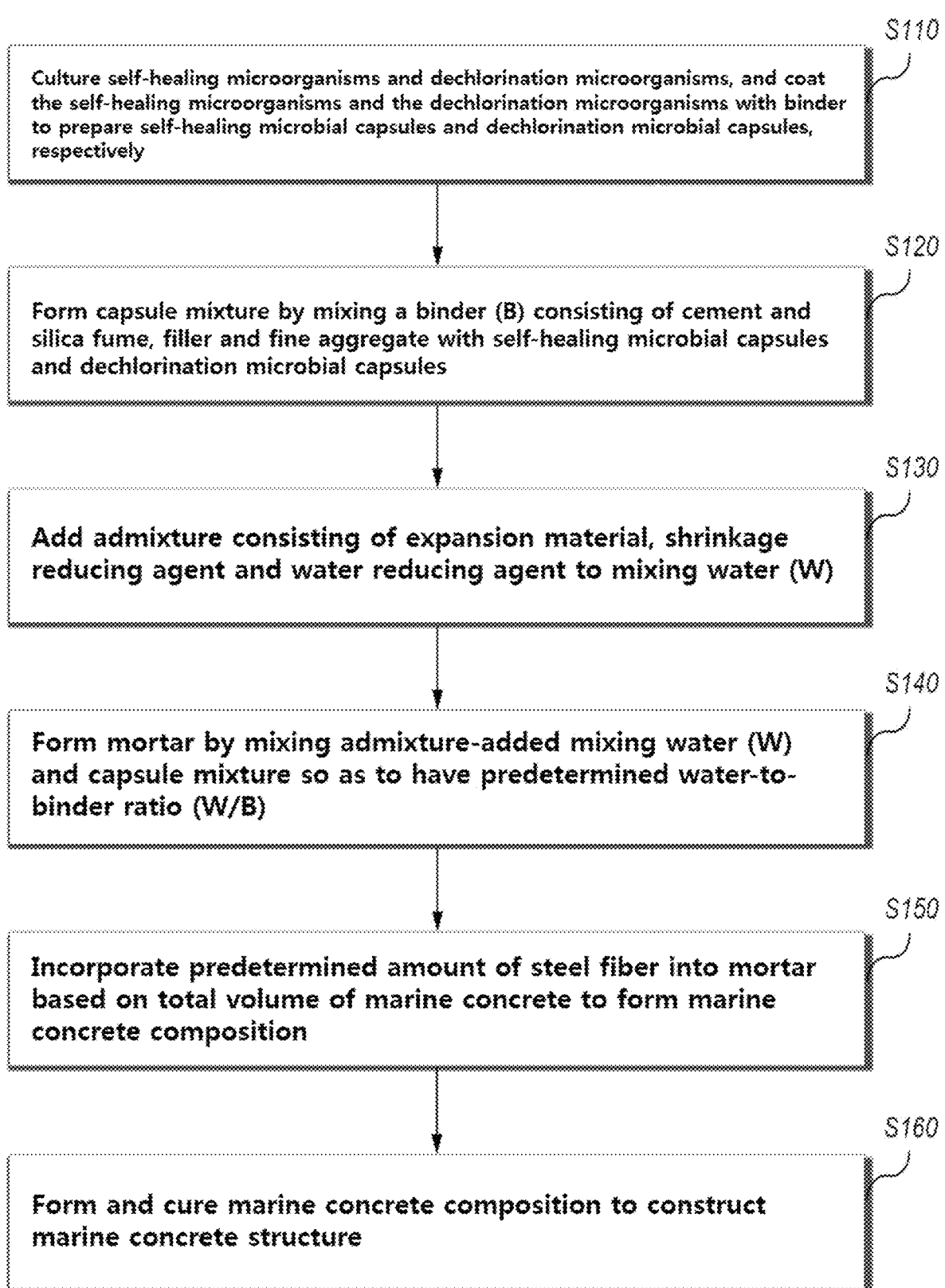

*S110*

Culture self-healing microorganisms and dechlorination microorganisms, and coat the self-healing microorganisms and the dechlorination microorganisms with binder to prepare self-healing microbial capsules and dechlorination microbial capsules, respectively

*S120*

Form capsule mixture by mixing a binder (B) consisting of cement and silica fume, filler and fine aggregate with self-healing microbial capsules and dechlorination microbial capsules

*S130*

Add admixture consisting of expansion material, shrinkage reducing agent and water reducing agent to mixing water (W)

*S140*

Form mortar by mixing admixture-added mixing water (W) and capsule mixture so as to have predetermined water-to-binder ratio (W/B)

*S150*

Incorporate predetermined amount of steel fiber into mortar based on total volume of marine concrete to form marine concrete composition

*S160*

Form and cure marine concrete composition to construct marine concrete structure

FIG. 12

MARINE CONCRETE COMPOSITION USING DECHLORINATION MICROORGANISM, AND CONSTRUCTION METHOD OF MARINE CONCRETE STRUCTURE FOR THE SAME

TECHNICAL FIELD

The present invention relates to a marine concrete composition, and more specifically, to a marine concrete composition using a dechlorination microorganism, which is applied to marine concrete to self-heal cracks through self-healing microbial capsules and remove chlorine through dechlorination microbial capsules as a marine concrete composition into which steel fiber and a capsule-type self-healing agent are incorporated, and a method for constructing a marine concrete structure using the same.

BACKGROUND ART

In general, marine concrete structures are structures installed in marine spaces, correspond to ship berthing facilities, docks, marine floating pontoons, marine piers, and the like, and require appropriate material selection and mixing design, and the like because they are often exposed to harsh environments such as seawater and low temperatures due to the nature of marine concrete structures that are directly exposed to the seawater environment, unlike general land structures.

The main causes of damage to such marine concrete structures include physical factors that act on concrete structures, such as wind, waves, currents, water pressure, friction caused by earth and sand, freeze-thaw effects, hydrodynamic pressure, icebergs, impacts, and the like, and further, as for chemical factors, the deterioration effect due to various chlorides contained in seawater is believed to be a major factor.

FIG. 1a is a schematic view illustrating a salt damage process of typical marine concrete, and FIG. 1b is a photograph illustrating corrosion of reinforcing bars due to salt damage in marine concrete.

As illustrated in FIG. 1a, most of the marine concrete structures constructed in Korea are general concrete containing coarse aggregate, and after cracks occur, chlorine ions supplied from seawater penetrate into the cracks and cause, for example, the corrosion of structural steel as illustrated in FIG. 1b and then cause a number of problems such as the coating thickness of concrete peeling or falling off while a passive film surrounding the structural steel is destroyed, thereby causing a decline in the performance of the structure.

Meanwhile, recently, various studies have been conducted around the world on self-healing concrete using microorganisms as a technology that repairs damaged areas using the metabolism of microorganisms when cracks occur in concrete by introducing microorganisms, spores, or carriers during the concrete mixing process.

FIG. 2 is a view for describing the concept of self-healing concrete, and FIG. 3 is a view for describing the self-healing of concrete according to a capsule-type self-healing agent.

As illustrated in FIG. 2, the basic principle of self-healing concrete is a mineral such as iron (Fe), manganese (Mn), magnesium (Mg), and calcium (Ca) is formed as a mineral along with carbonate ions ($CO_3^{2-}$), hydroxide ions ($OH^-$), complex oxide ions, and the like due to the metabolic process of microorganisms principle and this principle is used as the basis of technology for healing crack sites in concrete, which is currently applied limitedly to general concrete containing coarse aggregate.

Technology using microorganisms is being developed in connection with self-healing concrete. Technology using microorganisms uses the action of microorganisms to create minerals inside and outside their bodies, that is, biomineralization, and is performed by complexing inorganic components with biopolymers such as organic components such as proteins and polysaccharides and forming structures with precise order.

In particular, although the technology of forming self-healing concrete by mixing microorganisms that precipitate carbonates into cement is attracting attention, there is a problem in that it is difficult to maintain the activity of microorganisms in cement in a basic (alkaline) environment, and there is a problem in that even though minerals are formed from microorganisms when a structure cracks, it is difficult to heal relatively large crack sites within a short period of time.

To partially alleviate these problems, as illustrated in FIG. 3, a microbial culture solution may be prepared into capsules and added to concrete structures that are installed in water to minimize the loss of microorganisms during and after the preparation process.

However, in order to increase the healing effect of self-healing concrete according to the related art, a method of preparing microcapsules containing urea-degrading microorganisms has a problem in that preparation costs and time increase, and a problem in that it is difficult to mass-produce capsules.

Meanwhile, as the related art, Korean Patent No. 10-2209754 discloses an invention entitled "MICROORGANISM-BASED SELF-HEALING CONCRETE COMPOSITION AND METHOD FOR MANUFACTURING SELF-HEALING CONCRETE USING SAME," which is described with reference to FIG. 4 and FIG. 5.

FIG. 4 is a schematic view illustrating a concrete sample produced by a self-healing concrete composition according to the related art, and FIG. 5 is an operational flow view illustrating a method for manufacturing the self-healing concrete illustrated in FIG. 4.

Referring to FIG. 4, the self-healing concrete composition according to the related art includes a binder, aggregate, water, an AE agent, a microbial culture solution, urea, and calcium lactate.

Although cement may be used as a binder, other industrial by-products such as fly ash, bottom ash, and slag may also be used. In this case, the binder and water may be mixed at a weight ratio of approximately 1:1.

Sand may be used as the aggregate, and the aggregate may be mixed with the binder in almost the same weight. That is, the aggregate and the binder may be mixed at a weight ratio of approximately 1:1.

In addition, the AE agent creates an environment in which the microorganisms (M) in a microbial culture solution can survive by forming a large amount of microscopic voids (A) in concrete. In this case, the AE agent may be mixed in an amount of 0.3 to 1.0 wt % based on the weight of the binder (cement) of the concrete composition.

Urea is degraded by microorganisms in the microbial culture solution to produce carbonate ions ($CO_3^{2-}$). In other words, the urea-degrading microorganisms mixed in the microbial culture solution degrade urea to produce carbonate ions ($CO_3^{2-}$), which react with calcium ions ($Ca^{2+}$) in the concrete, thereby achieving a self-healing action by generating calcium carbonate ($CaCO_3$), that is, the main component of calcite or limestone to fill voids and cracks in concrete.

Calcium lactate can produce a large amount of calcium carbonate ($CaCO_3$) by additionally providing calcium ions ($Ca^{2+}$) to which carbonate ions ($CO_3^{2-}$) produced by urea-degrading microorganisms in concrete can bind.

Referring to FIG. 5, in the method for manufacturing self-healing concrete according to the related art, a microbial culture solution is first prepared (S11). Here, the microbial culture solution is prepared by adding 2 wt % of each of tryptic soy broth (TSB) and urea based on the weight of distilled water to distilled water, and then inoculating urea-degrading microorganisms into the mixed culture solution and culturing the resulting mixture. In this case, the microorganisms may be inoculated at a temperature of 25 to 30° C., and then cultured for 1 day.

Next, cement as a binder, aggregate, powdered urea and calcium lactate are dry-mixed to prepare a mixture (S12), and then water, the microbial culture solution and an AE agent are mixed with the dry-mixed mixture (S13) to produce a concrete composition (S14). In this case, the AE agent is mixed in an amount of 0.3 to 1.0 wt % based on the weight of the binder (cement). Since the AE agent is added in a very small amount in the concrete composition as described above, the AE agent is first incorporated into the microbial culture solution in Step S13 without being dry-mixed with the cement, and then may be mixed with the dry-mixed mixture.

Next, the concrete composition thus prepared is placed inside a space formed by formwork and cured to produce self-healing concrete (S15).

In other words, in the case of a self-healing concrete composition according to the related art, by mixing a microbial culture solution, urea, and calcium lactate with a binder such as cement, when concrete cracks are generated, a large amount of calcium carbonate may be formed by microorganisms to self-heal crack sites.

According to the self-healing concrete composition according to the related art, through a self-healing composition into which microorganisms are incorporated by incorporating a binder, aggregate, water, an AE agent (water-reducing agent), urea, calcium lactate, and a microbial culture solution (spore-forming microorganism *Sporosarcina pasteurii*), calcium carbonate may be generated through the metabolic phenomenon of microorganisms in concrete cracks or internal voids to heal crack sites.

However, in the case of the self-healing concrete composition according to the related art, the binder and water are mixed at a weight ratio of approximately 1:1 and applied to the concrete, and there is a problem in that the durability of marine concrete against salt damage deteriorates.

Meanwhile, as another related art, Korean Patent No. 10-2047384 discloses an invention titled "Concrete self-healing microcapsules using microorganisms, a method for producing the same, and a self-healing concrete composition containing the microcapsules," which will be described with reference to FIGS. 6a and 6b.

FIG. 6a is a view illustrating the structure of a concrete self-healing microcapsule according to the related art, and FIG. 6b is a schematic view for describing the self-healing action of the urea-degrading microorganisms and the urea-non-degrading microorganisms incorporated into the microcapsule illustrated in FIG. 6a.

Referring to FIG. 6a, the concrete self-healing microcapsules are incorporated into concrete to automatically generate calcium carbonate when cracks occur in the concrete and exhibit a self-healing action, and include a core produced by mixing spores formed by co-culturing urea-degrading microorganisms 11 and urea-non-degrading microorganisms 12 with an oil 13 and yeast 14; and a shell 20 surrounding the core 10.

The shell 20 is a polymer membrane with a thickness of approximately 0.01 to 30 μm, and may consist of a melamine-formaldehyde polymer, a urea-formaldehyde polymer, polyurethane, a urea-melamine-formaldehyde polymer, silica, a polyurea resin, a polyamide resin, alginic acid, gelatin, gum arabic, an acrylic acid-based resin, a polymethyl methacrylate resin, a polyvinyl alcohol resin, cellulose, and the like. It is preferred that such a shell 20 has appropriate mechanical properties that make it difficult to break during the handling process and easy to break when cracks occur.

The overall size (diameter) of the microcapsules is approximately 1 to 700 μm, and as the microcapsules are ruptured by cracks in the concrete, the urea-degrading microorganism 11 present in the core 10 produces carbonate ions ($CO_3^{2-}$), and the carbonate ions react with calcium ions ($Ca^{2+}$) in the concrete to produce calcium carbonate, thereby exhibiting a self-healing action. In this case, the urea-non-degrading microorganism 12 present in the core 10 does not have the action of producing carbonate ions ($CO_3^{2-}$) but acts to increase the amount of calcium carbonate precipitated by providing a nucleation site for producing calcium carbonate.

The urea-degrading microorganism 11 degrades urea in the concrete to produce carbonate ions ($CO_3^{2-}$), and the carbonate ions ($CO_3^{2-}$) react with calcium ions ($Ca^{2+}$) in the concrete to fill cracks in the concrete by generating calcium carbonate ($CaCO_3$), that is, the main component of calcite or limestone.

The urea-non-degrading microorganism 12 provides a nucleation site where carbonate ions ($CO_3^{2-}$) and calcium ions ($Ca^{2+}$) degraded by the urea-degrading microorganism (11) can bind, thereby acting to increase the amount of calcium carbonate ($CaCO_3$) precipitated.

Self-healing materials utilize existing microorganisms contain only urea-degrading microorganisms, but as illustrated in FIG. 6B, the cell surfaces of urea-degrading microorganisms are supersaturated with precipitated calcium carbonate, making them unable to absorb surrounding nutrients, and as time passes, the action of producing carbonate ions ($CO_3^{2-}$) through urea degradation cannot be performed, so that the amount of calcium carbonate precipitated decrease.

In other words, the concrete self-healing microcapsules according to the related art are made by incorporating spores formed by co-culturing urea-degrading microorganisms and urea-non-degrading microorganisms, so that a large amount of calcium carbonate may be produced by urea-degrading microorganisms when cracks occur in concrete to heal the crack site.

According to concrete self-healing microcapsules according to the related art, spores formed by co-culturing urea-degrading microorganisms and urea-non-degrading microorganisms are incorporated into the microcapsules and protected by a shell, so that it is possible to maintain the activity of microorganisms in concrete in a basic (alkaline) environment, and it is possible to prevent a phenomenon in which the amount of microorganisms expressed due to the pressure caused by hydrate production during hardening of concrete is reduced.

In addition, urea-non-degrading microorganisms are incorporated together with urea-degrading microorganisms at a predetermined ratio, and as a result, the urea-non-degrading microorganisms provide a nucleation site where carbonate ions ($CO_3{}^{2-}$) and calcium ions ($Ca^{2+}$) degraded by urea-degrading microorganisms can bind, so that it is possible to significantly improve the self-healing performance of concrete when cracks occur by increasing the amount of calcium carbonate ($CaCO_3$) precipitated.

However, concrete self-healing microcapsules according to the related art have a problem in that the durability of marine concrete against salt damage deteriorates.

Meanwhile, although ultra-high-performance concrete (UHPC), which has recently been developed using micro- or nano-sized materials, has mechanical performance such as a compressive strength of 80 to 180 MPa, a flexural strength of 15 MPa or more, a direct tensile strength of 7 MPa or more, a durable lifespan of 100 to 200 years, and a shrinkage strain of 700 or less, there is a need for developing a technology which fundamentally removes chlorine in the case of cracks occurring due to vibrations and cracks over time when ultra-high-performance concrete (UHPC) is placed in a marine environment.

Furthermore, as described above, self-healing concrete is currently applied limitedly to general concrete including coarse aggregate, but it needs to be easily applied even to ultra-high-performance concrete (UHPC) or a high-performance fiber reinforced cementitious composite (HPFRCC).

PRIOR ART LITERATURE

Patent Literature (Patent Document 0001) Korean Patent No. 10-2209754 (registration date: Jan. 25, 2021), Title of the Invention: "MICROORGANISM-BASED SELF-HEALING CONCRETE COMPOSITION AND METHOD FOR MANUFACTURING SELF-HEALING CONCRETE USING SAME"

(Patent Document 0002) Korean Patent No. 10-2047384 (registration date: Nov. 15, 2019), Title of the Invention: "CONCRETE SELF-HEALING MICROCAPSULES USING MICROORGANISMS, METHOD FOR MANUFACTURING THE SAME, AND SELF-HEALING CONCRETE COMPOSITION CONTAINING THE MICROCAPSULES"

(Patent Document 0003) Korean Patent No. 10-1448068v (registration date: Sep. 30, 2014), Title of the Invention: "CONCRETE USING MICROBIAL CAPSULES AND METHOD FOR MANUFACTURING THE SAME"

(Patent Document 0004) Korean Patent No. 10-2324112 (registration date: Nov. 3, 2021), Title of the Invention: "HALOPHILIC SLIME FORMING BACTERIUM-BASED SECTION REPAIR MATERIAL"

(Patent Document 0005) Japanese Patent Application Laid-Open No. 2019-213307 (registration date: Dec. 12, 2019), Title of the Invention: "CONCRETE POLE AND METHOD OF MANUFACTURING SAME"

(Patent Document 0006) US Patent Publication No. 2014-0248681 (registration date: Sep. 4, 2014), Title of the Invention: "MICROCAPSULES AND CONCRETE CONTAINING THE SAME"

DESCRIPTION

Technical Problem

A technical problem addressed by the present invention to solve the above-described problems is to provide a marine concrete composition using dechlorination microorganisms capable of removing chlorine generated by seawater through an electrical method by allowing electrons emitted from electricity-generating microorganisms to flow through steel fibers incorporated into ultra-high-performance concrete or high-performance fiber reinforced concrete through a dechlorination microbial capsule carrier and capable of self-healing concrete crack sites through a self-healing microbial capsule carrier, and a method for constructing a marine concrete structure using the same.

Another technical problem addressed by the present invention is to provide a marine concrete composition using dechlorination microorganisms capable of fundamentally solving the problem of reduced durability against salt damage of ultra-high-performance concrete or high-performance fiber reinforced concrete for application in marine construction environments through a dechlorination microbial capsule carrier, and a method for constructing a marine concrete structure using the same.

Technical Solution

As a means for addressing the above-described technical problems, the marine concrete composition using dechlorination microorganisms according to the present invention is a marine concrete composition formed of ultra-high-performance concrete (UHPC), wherein the ultra-high-performance concrete composition includes: 100 parts by weight of cement as a binder (B); as a binder, 10 to 30 parts by weight of silica fume; 100 to 140 parts by weight of fine aggregate; 15 to 30 parts by weight of a filler; 15 to 25 parts by weight of mixing water (W) based on 100 parts by weight of the cement; 1 to 3 parts by weight of an expansion material; 1 to 3 parts by weight of a shrinkage reducing agent; and 4 to 7 parts by weight of a water reducing agent, and water, which is the mixing water (W), and the binder (B) are mixed such that a ratio (W/B) is 0.2 or less; 1.5 to 3% of steel fiber is incorporated based on the total volume of the ultra-high-performance concrete; and 0.5 to 2% of self-healing microbial capsules and 1 to 5% of dechlorination microbial capsules based on the total volume of the ultra-high-performance concrete are incorporated, the self-healing microbial capsule is a carrier of spore-forming microorganisms for self-healing, and the dechlorination microbial capsule is a carrier of electricity-generating microorganisms for removing chlorine.

Here, the self-healing microbial capsule may self-heal ultra-high-performance concrete through calcium carbonate ($CaCO_3$) produced by spore-forming microorganisms capable of self-healing, and the dechlorination microbial capsule may remove chlorine ($Cl^-$) produced by salt damage through an electrical method that allows electrons ($e^-$) emitted from electricity-generating microorganisms to flow through steel fibers incorporated into the ultra-high-performance concrete.

Here, the self-healing microbial capsules may have a size of 1 μm to 400 μm, and the dechlorination microbial capsules may have a size of 50 μm to 400 μm.

Here, the self-healing microorganism may be *Bacillus pasteurii* or *Sporosarcina pasteurii* having the ability to degrade urea.

Here, the electricity-generating microorganism may be *Geobacter.*

Meanwhile, as another means for addressing the above-described technical problems, the marine concrete composition using dechlorination microorganisms according to the present invention is a marine concrete composition formed of a high-performance fiber reinforced cementitious composite (HPFRCC), wherein the high-performance fiber reinforced cementitious composite composition includes: 100 parts by weight of cement as a binder (B); as a binder, 10 to 30 parts by weight of silica fume; 100 to 140 parts by weight of fine aggregate; 15 to 30 parts by weight of a filler; 22 to 64 parts by weight of mixing water (W); 1 to 3 parts by weight of an expansion material; 1 to 3 parts by weight of a water reducing agent; and 10 to 30 parts by weight of a water reducing agent, and water, which is the mixing water (W), and the binder (B) are mixed such that a ratio (W/B) is 0.2 to 0.4; 1.5 to 3% of steel fiber is incorporated based on the total volume of the high-performance fiber reinforced cementitious composite; and 0.5 to 2% of self-healing microbial capsules and 1 to 5% of dechlorination microbial capsules based on the total volume of the high-performance fiber reinforced cementitious composite are incorporated, the self-healing microbial capsule is a carrier of spore-forming microorganisms for self-healing, and the dechlorination microbial capsule is a carrier of electricity-generating microorganisms for removing chlorine.

Here, the self-healing microbial capsule may self-heal the cementitious composite through calcium carbonate ($CaCO_3$) produced by spore-forming microorganisms capable of self-healing, and the dechlorination microbial capsule may remove chlorine ($Cl^-$) produced by salt damage through an electrical method that allows electrons ($e^-$) emitted from electricity-generating microorganisms to flow through steel fibers incorporated into the cementitious composite.

Meanwhile, as still another means for addressing the technical problems, a method for constructing a marine concrete structure using dechlorination microorganisms according to the present invention includes: a) culturing self-healing microorganisms and dechlorination microorganisms and coating the self-healing microorganisms and the dechlorination microorganisms with a binder to prepare self-healing microbial capsules and dechlorination microbial capsules, respectively; b) forming a capsule mixture by mixing a binder (B) consisting of cement and silica fume, a filler and fine aggregate with the self-healing microbial capsules and the dechlorination microbial capsules; c) adding an admixture consisting of an expansion material, a shrinkage reducing agent and a water reducing agent to mixing water (W); d) forming a mortar by mixing the admixture-added mixing water (W) and the capsule mixture so as to have a predetermined water-to-binder ratio (W/B); e) incorporating a predetermined amount of steel fiber into the mortar based on the total volume of marine concrete to form a marine concrete composition; and f) forming and curing the marine concrete composition to construct a marine concrete structure.

Here, the marine concrete composition may be an ultra-high-performance concrete composition or a high-performance fiber reinforced cementitious composite composition with a compressive strength of 120 MPa to 180 MPa.

Advantageous Effects

According to the present invention, concrete crack sites can be self-healed through a self-healing microbial capsule carrier, and electrons emitted from electricity-generating microorganisms can be allowed to flow through steel fibers incorporated into ultra-high-performance concrete or high-performance fiber reinforced concrete through a dechlorination microbial capsule carrier to easily remove chlorine generated by seawater through an electrical method.

According to the present invention, the problem of reduced durability against salt damage of ultra-high-performance concrete or high-performance fiber reinforced concrete for application to marine construction environments can be fundamentally prevented through a dechlorination microbial capsule carrier.

BRIEF DESCRIPTION OF THE DRAWINGS

FIG. 6b is a schematic view for describing the self-healing action of the urea-degrading microorganisms and the urea-non-degrading microorganisms incorporated into the microcapsule illustrated in FIG. 6a.

FIG. 10 is a view illustrating the blending of ultra-high-performance concrete (UHPC) as a marine concrete composition using the dechlorination microorganisms according to a first exemplary embodiment of the present invention.

FIG. 11 is a view illustrating the blending of a high-performance fiber reinforced cementitious composite (HP-FRCC) as a marine concrete composition using the dechlorination microorganisms according to a second exemplary embodiment of the present invention; and FIG. 12 is an operational flow diagram illustrating a method for constructing a marine concrete structure using dechlorination microorganisms according to an exemplary embodiment of the present invention.

MODE FOR INVENTION

Figure 1A:
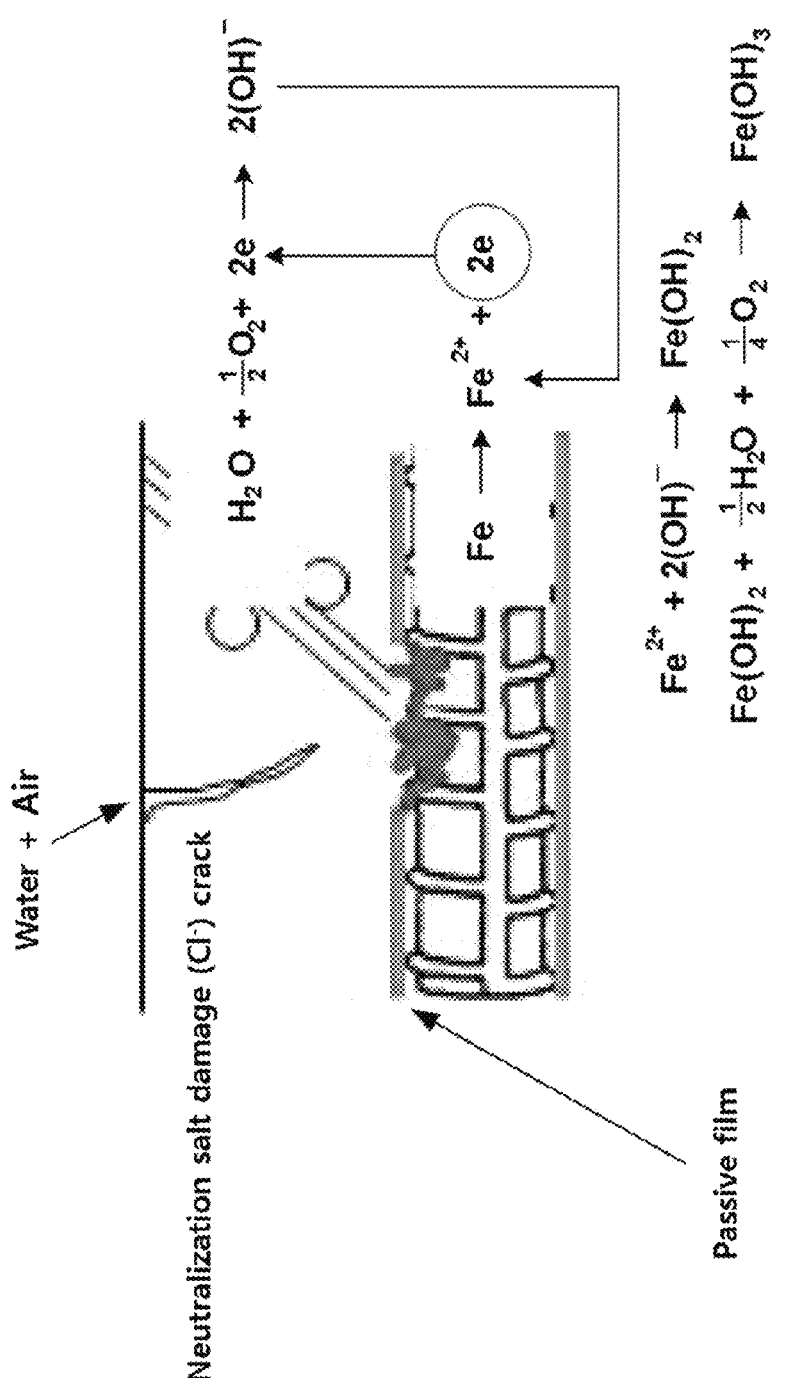
FIG. 1a is a schematic view illustrating a salt damage process of typical marine concrete.
Figure 1B:
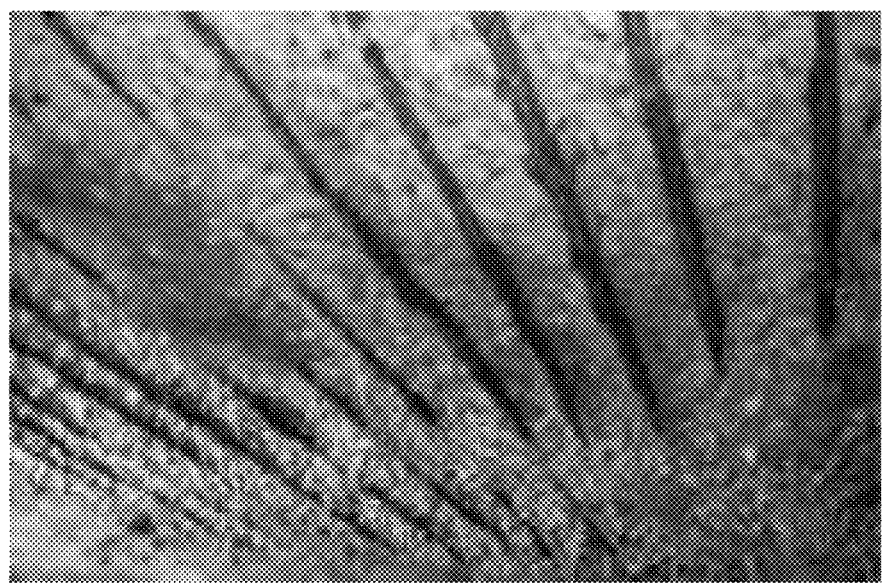
FIG. 1b is a photograph illustrating corrosion of reinforcing bars due to salt damage in marine concrete.
Figure 2:
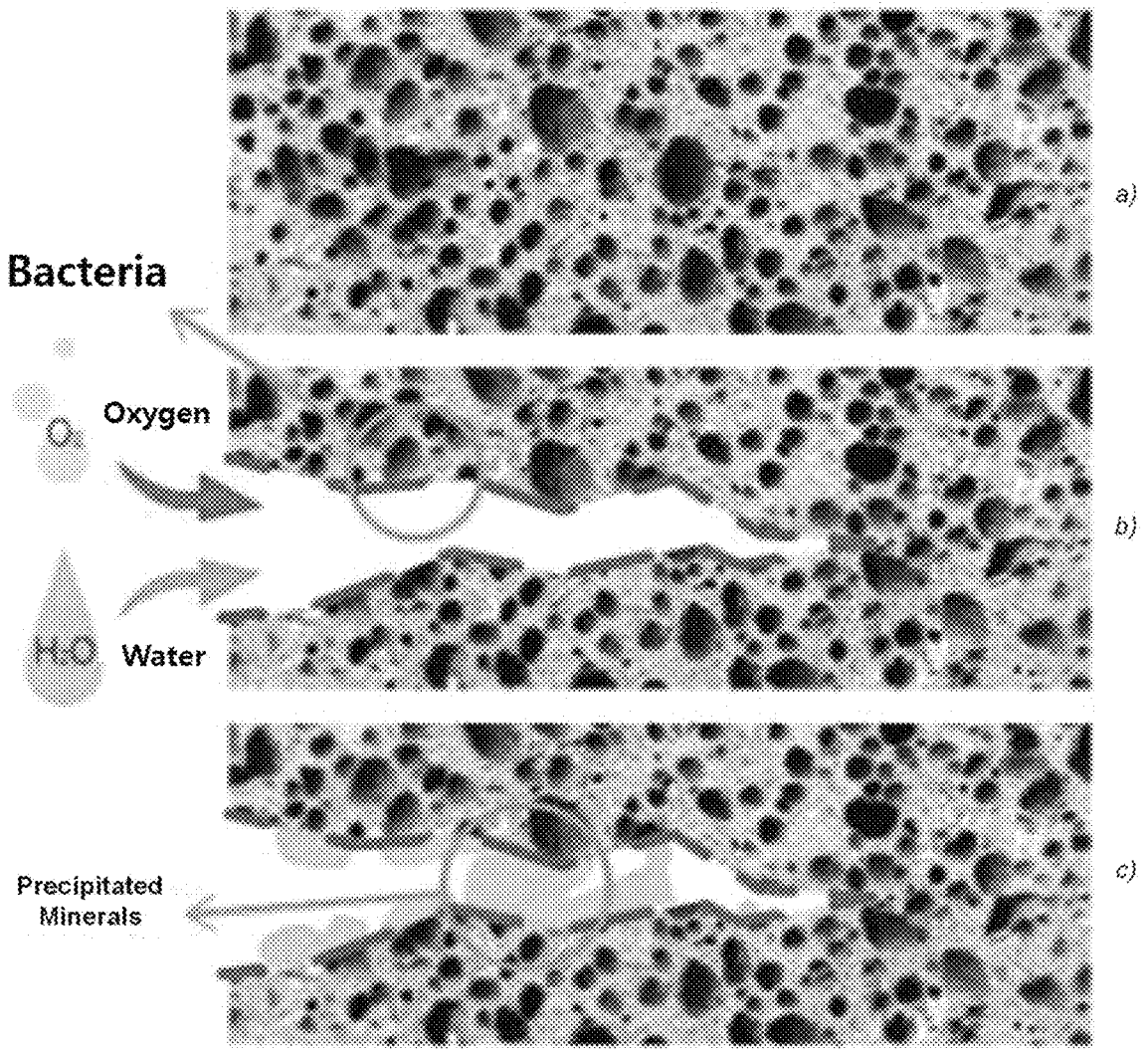
FIG. 2 is a view for describing the concept of self-healing concrete.
Figure 3:
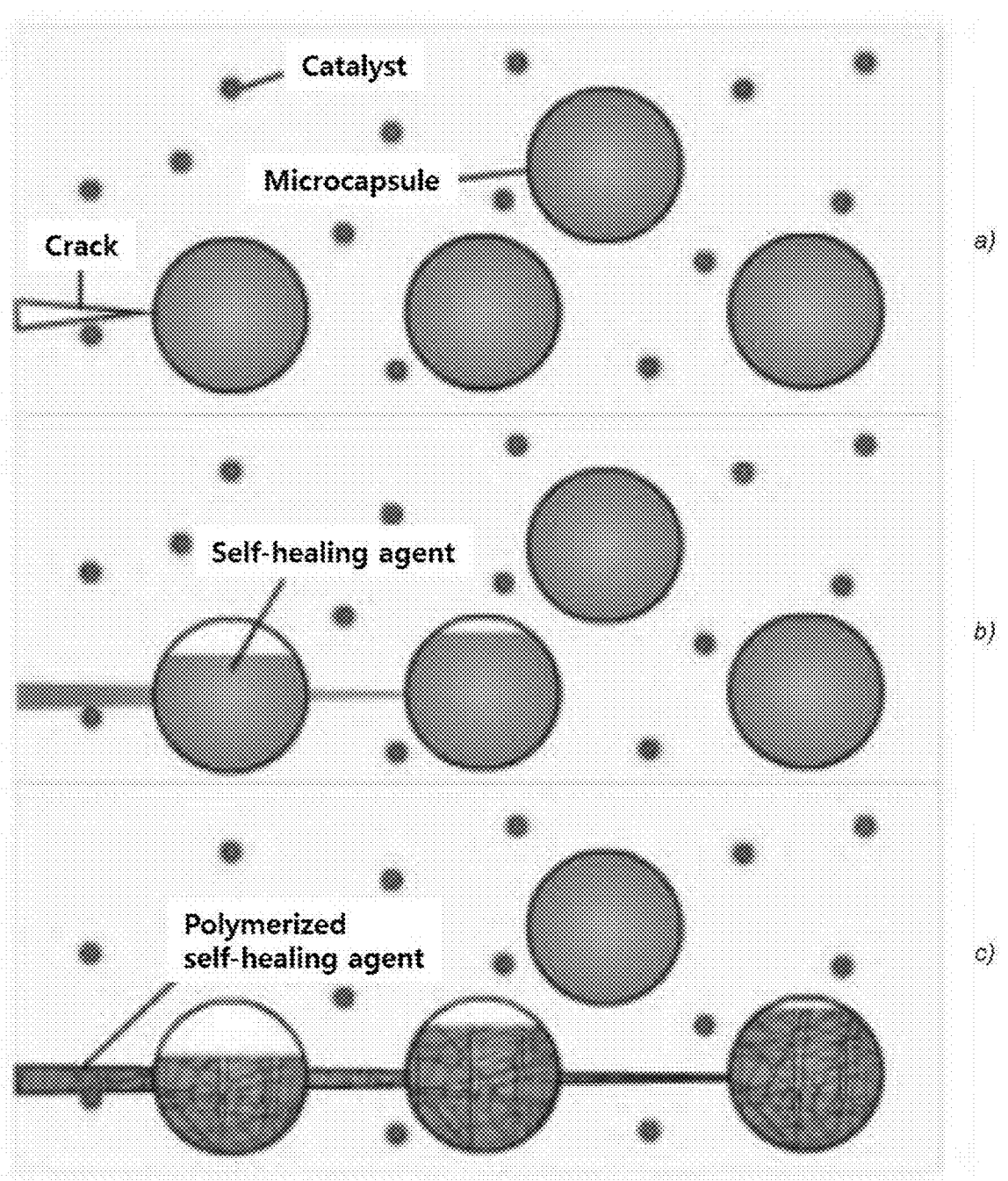
FIG. 3 is a view for describing the self-healing of concrete according to a capsule-type self-healing agent.
Figure 4:
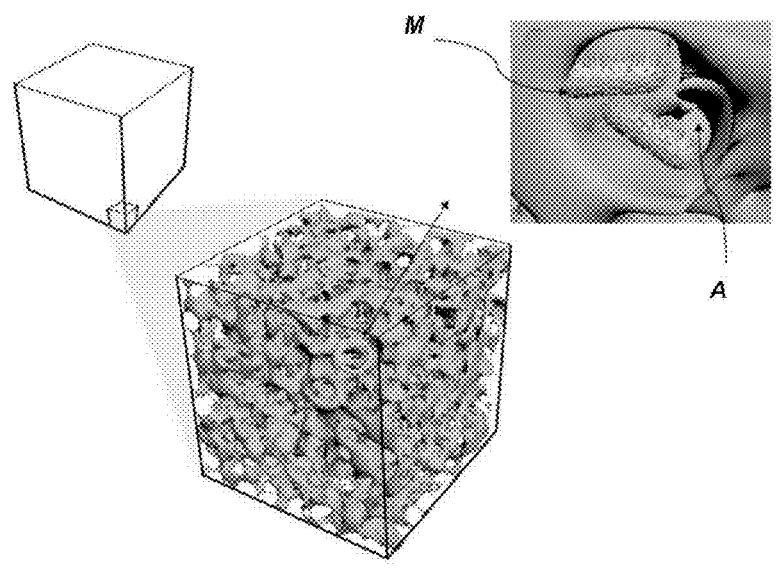
FIG. 4 is a schematic view illustrating a concrete sample prepared using a self-healing concrete composition according to the related art.
Figure 5:
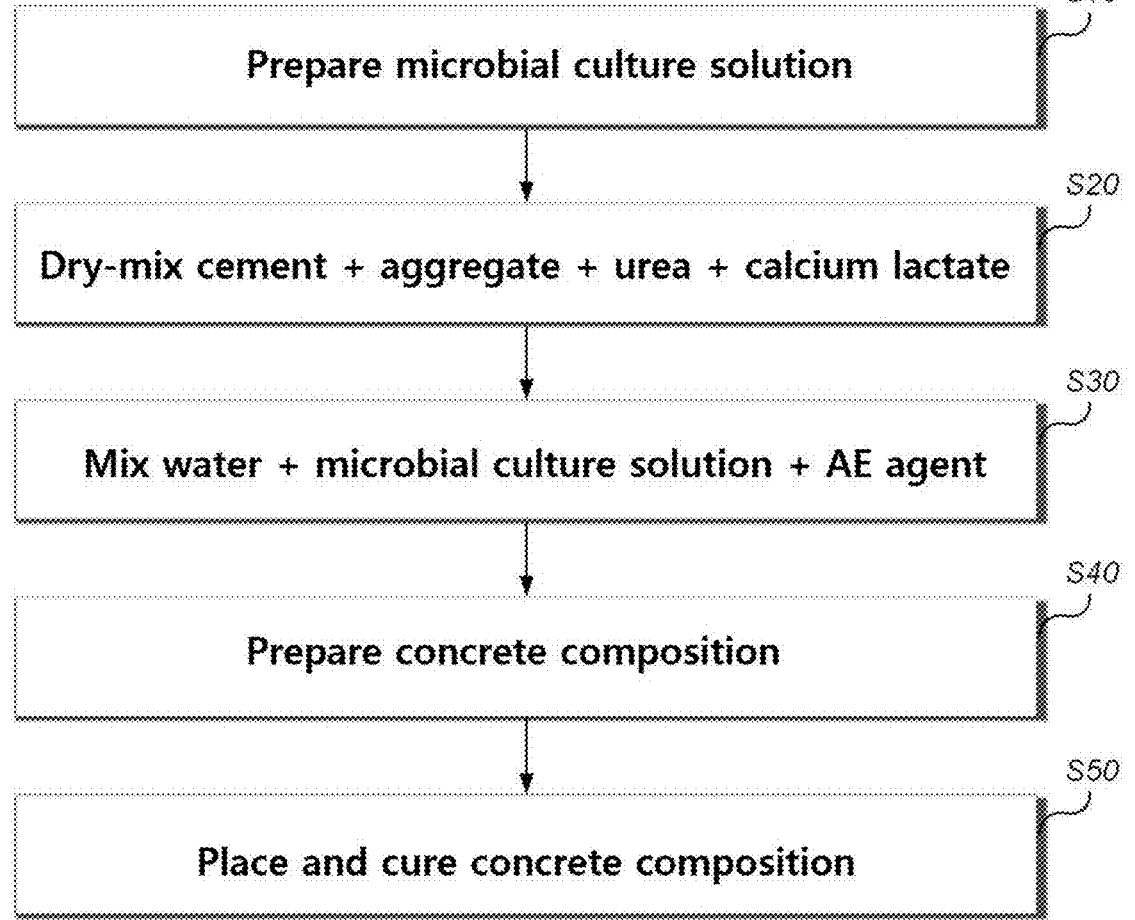
FIG. 5 is an operational flow diagram illustrating a method for manufacturing the self-healing concrete illustrated in FIG. 4.
Figure 6A:
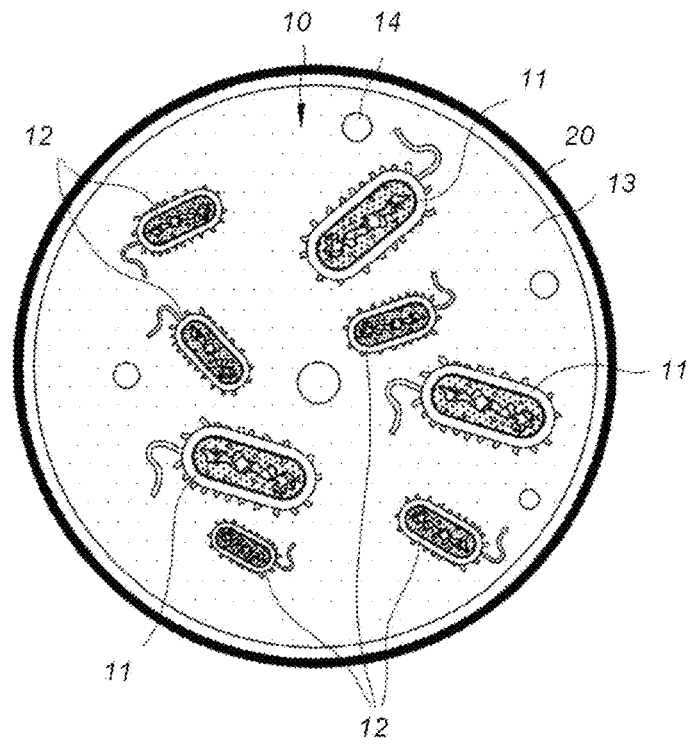
FIG. 6a is a view illustrating the structure of a concrete self-healing microcapsule according to the related art.
Figure 6B:
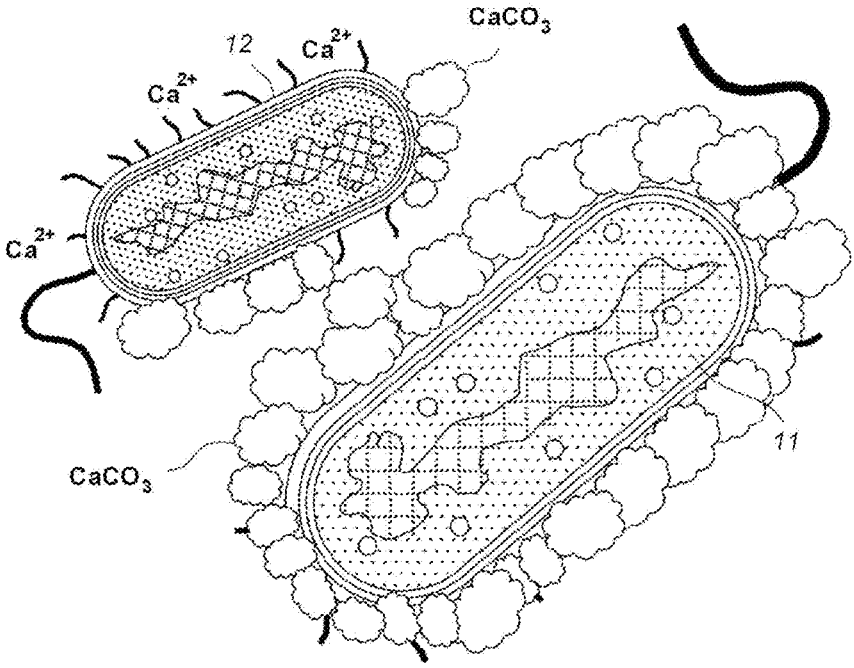

Hereinafter, exemplary embodiments of the present invention will be described in detail with reference to the accompanying drawings such that a person with ordinary skill in the art to which the present invention pertains can easily carry out the present invention. However, the present invention may be implemented in various different forms and is not limited to the exemplary embodiments described herein. In addition, in order to clearly describe the present invention, portions that are not related to the description are omitted in the drawings, and like reference numerals are added to like portions throughout the specification.

Throughout the present specification, when one part "includes" one constituent element, unless otherwise specifically described, this does not mean that another constituent element is excluded, but means that another constituent element may be further included.

[Chlorine Removal Principle of Capsule-Type Self-Healing Agent]

Figure 7:
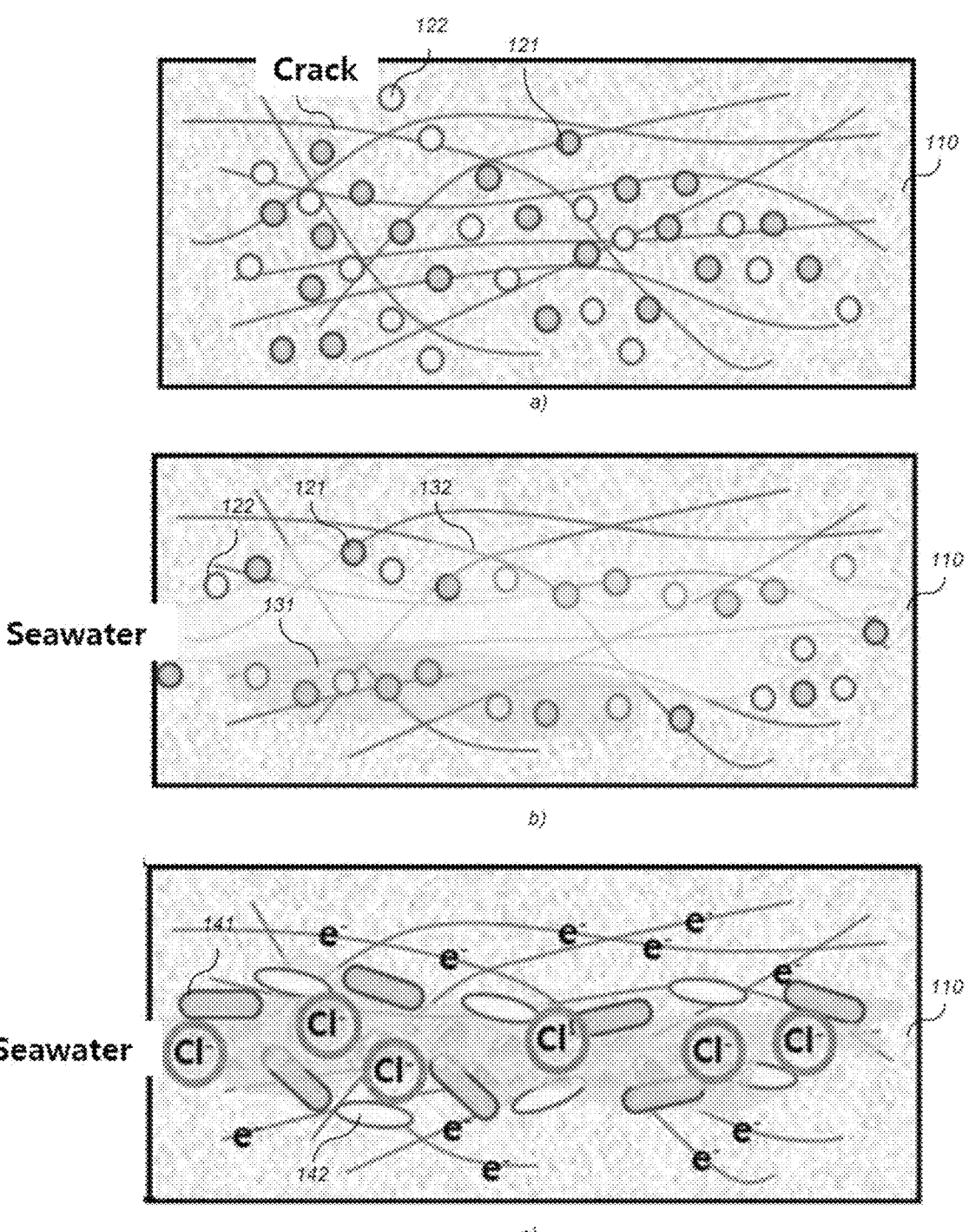
FIG. 7 is a set of views specifically illustrating a capsule-type self-healing agent into which dechlorination microorganisms are injected in marine concrete using dechlorination microorganisms according to an exemplary embodiment of the present invention.

FIG. 7 is a set of views specifically illustrating a capsule-type self-healing agent into which dechlorination microorganisms are injected in marine concrete using dechlorination microorganisms according to an exemplary embodiment of the present invention.

Referring to FIG. 7, in the case of marine concrete using dechlorination microorganisms according to an exemplary embodiment of the present invention, by incorporating self-healing microbial capsules 121 and dechlorination microbial capsules 122, it is possible to remove chlorine generated by salt damage through an electrical method in which electricity-generating microorganisms allow electrons (e⁻) generated during the production process of calcium carbonate (CaCO₃) produced by microorganisms capable of self-healing in ultra-high-performance concrete (UHPC) or a high-performance fiber reinforced cementitious composite (HP-FRCC) containing steel fibers to flow through the steel fibers.

Specifically, as illustrated in a) of FIG. 7, for the purpose of self-healing cracks and removing chlorine in marine concrete 110 such as ultra-high-performance concrete (UHPC) or a high-performance fiber reinforced cementitious composite (HPFRCC), self-healing microbial capsules 121 and dechlorination microbial capsules 122 are incorporated. Further, as illustrated in b) of FIG. 7, as seawater permeates into the marine concrete 110, the self-healing microbial capsules 121 and the dechlorination microbial capsules 122 allow self-healing microorganisms to grow as metabolites 131 and nutrients 132 are supplied, and in addition, as illustrated in c) of FIG. 7, cracks may be healed by spore-forming microorganisms which are self-healing microorganisms 141, such as *Sporosarcina pasteurii*, and chlorine may be removed by electricity-generating microorganisms 142, such as *Geobacter*.

Figure 8:
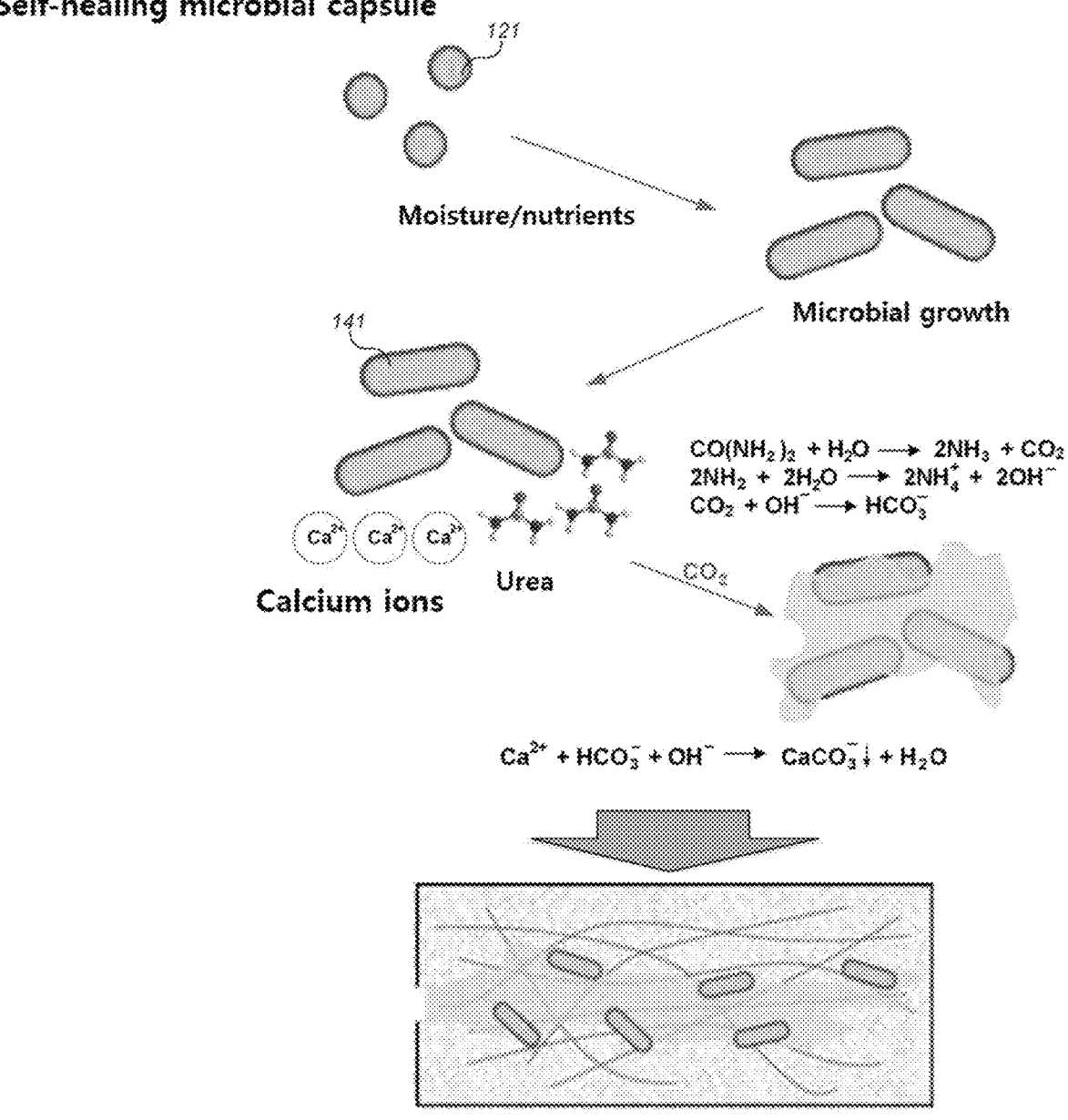
FIG. 8 is a view specifically illustrating the self-healing mechanism of the capsule-type self-healing agent in marine concrete using the dechlorination microorganisms according to an exemplary embodiment of the present invention.

Meanwhile, FIG. 8 is a view specifically illustrating the self-healing mechanism of the capsule-type self-healing agent in marine concrete using the dechlorination microorganisms according to an exemplary embodiment of the present invention.

Referring to FIG. 8, in the marine concrete using dechlorination microorganisms according to an exemplary embodiment of the present invention, the self-healing microbial capsule 121 is a carrier of microorganisms used in the self-healing concrete, and in this case, self-healing microorganisms include *Bacillus pasteurii* and *Sporosarcina pasteurii*, which have the ability to degrade urea, and include microorganisms used for concrete crack repair and limestone repair.

For example, *Bacillus pasteurii* includes *Bacillus licheniformis, Bacillus pseudofirms, Bacillus cohnii, Bacillus cereus, Bacillus subtilis, Bacillus sphaericus, Bacillus lentus*, and the like.

Furthermore, *Sporosarcina pasteurii* is a Gram-positive bacterium, has a *Bacillus* morphology and can grow in seawater and under high pH conditions and various harsh conditions. That is, calcium carbonate (CaCO₃) is crystallized through a combination of *Sporosarcina pasteurii*, which supplies calcium (Ca) through microbial metabolism, and urea, and is also produced as a calcium carbonate polymer using *Bacillus licheniformis*.

Figure 9:
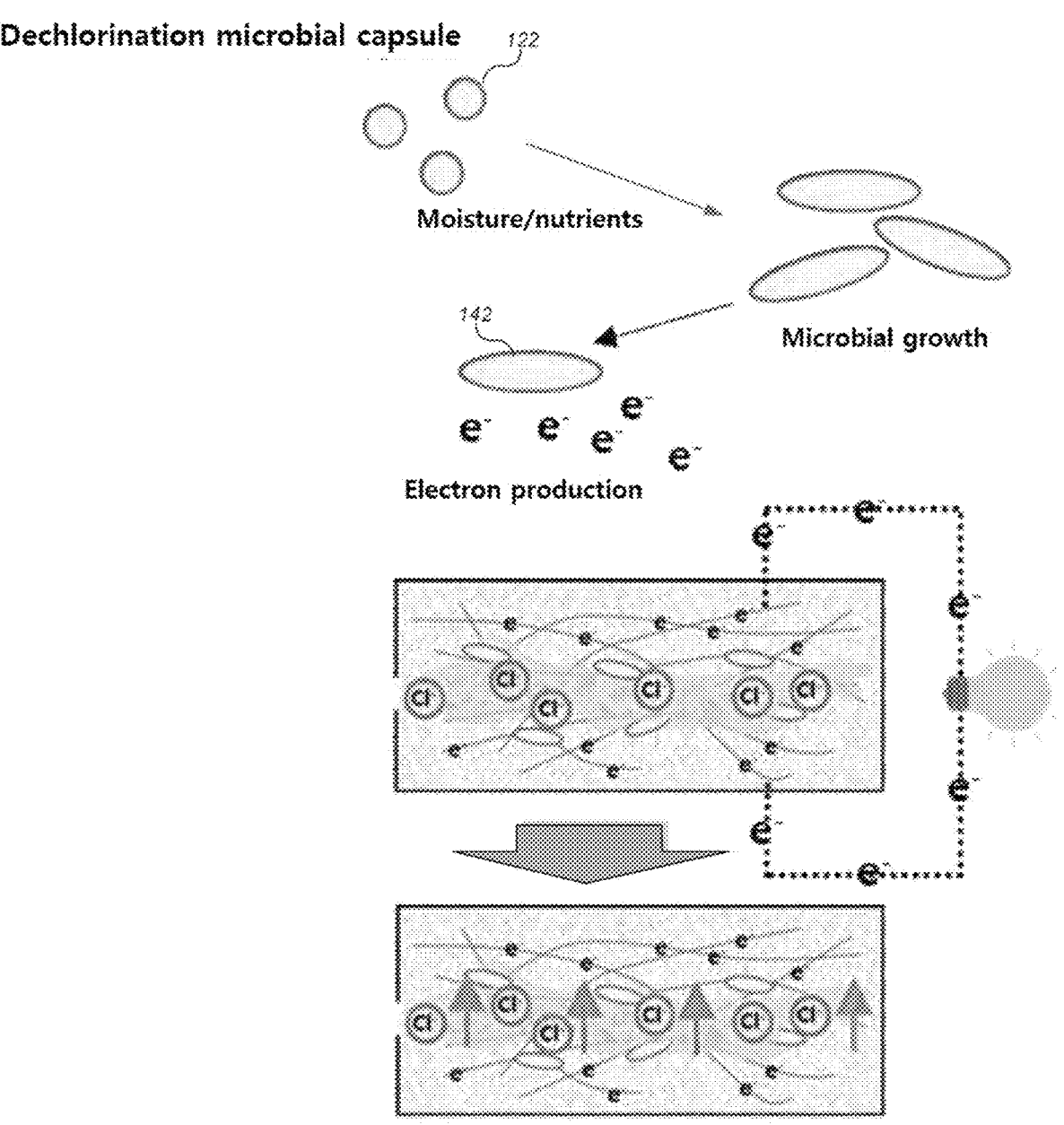
FIG. 9 is a view for specifically describing the chlorine-removal mechanism of the capsule-type self-healing agent in marine concrete using the dechlorination microorganisms according to an exemplary embodiment of the present invention.

FIG. 9 is a view for specifically describing the chlorine-removal mechanism of the capsule-type self-healing agent in marine concrete using the dechlorination microorganisms according to an exemplary embodiment of the present invention.

Referring to FIG. 9, in the marine concrete using dechlorination microorganisms according to an exemplary embodiment of the present invention, the dechlorination microbial capsule 122 is a carrier of the dechlorination microorganisms in the marine concrete using dechlorination microorganisms according to an exemplary embodiment of the present invention, and through an electrical method that allows electrons (e⁻) emitted from *Geobacter*, the aforementioned electricity-generating microorganism 142, to flow through steel fibers incorporated into ultra-high-performance concrete or a high-performance fiber reinforced cementitious composite, chlorine ions (Cl⁻) generated by salt damage may be easily removed.

In other words, in the case of marine concrete using dechlorination microorganisms according to an exemplary embodiment of the present invention, as not only self-healing microbial capsules 121 for self-healing but also dechlorination microbial capsules 122 for removing chlorine are incorporated together to form marine concrete, it is possible to self-heal cracks and increase durability against salt damage through chlorine removal.

Meanwhile, the marine concrete using dechlorination microorganisms according to an exemplary embodiments of the present invention may be ultra-high-performance concrete (UHPC) or a high-performance fiber reinforced cementitious composite (HPFRCC), and will be described as First Example and Second Example, respectively.

First Example: Marine Concrete (Ultra-High-Performance Concrete) Composition Using Dechlorination Microorganisms FIG. 10 is a view illustrating the blending of ultra-high-performance concrete (UHPC) as a marine concrete composition using the dechlorination microorganisms according to a first exemplary embodiment of the present invention.

Referring to FIG. 10, the marine concrete composition using dechlorination microorganisms according to a first example of the present invention is a marine concrete composition formed of ultra-high-performance concrete (UHPC), wherein the ultra-high-performance concrete (UHPC) composition includes: 100 parts by weight of cement as a binder (B); as a binder, 10 to 30 parts by weight of silica fume; 100 to 140 parts by weight of fine aggregate; 15 to 30 parts by weight of a filler; 15 to 25 parts by weight of mixing water (W) based on 100 parts by weight of the cement; 1 to 3 parts by weight of an expansion material; 1 to 3 parts by weight of a shrinkage reducing agent; and 4 to 7 parts by weight of a water reducing agent, and for example, the fine aggregate may be quartz sand with a particle diameter of 0.5 mm or less and the filler may be a quartz powder with an average particle diameter of 4 μm, but are not limited thereto. In addition, the water reducing agent may be a polycarboxylic acid-based high-performance water reducing agent but is not limited thereto.

Furthermore, water, which is the mixing water (W), and the binder (B) are mixed such that the ratio (W/B) is 0.2 or less. That is, in the case of the marine concrete composition using dechlorination microorganisms according to the first example of the present invention, water and the binder (B)

are mixed such that the ratio (W/B) of water to binder (B) is adjusted so as to be suitable for ultra-high-performance concrete (UHPC).

Further, 1.5 to 3% of steel fiber is incorporated into the ultra-high-performance concrete based on the total volume of the ultra-high-performance concrete. That is, 1.5 to 3%, optimally 2 to 2.5% of steel fiber as electrically conductive fiber may be incorporated, based on the total volume of the ultra-high-performance concrete.

In addition, 0.5 to 2% of self-healing microbial capsules 121 based on the total volume of the ultra-high-performance concrete and 1 to 5% of dechlorination microbial capsules 122 based on the total volume of the ultra-high-performance concrete are incorporated, the self-healing microbial capsule 121 may be a carrier of spore-forming microorganisms for self-healing, and the dechlorination microbial capsule 122 may be a carrier of electricity-generating microorganisms for removing chlorine. In this case, the self-healing microbial capsule 121 may be optimally incorporated at 1 to 1.5%, and the dechlorination microbial capsule 122 may be optimally incorporated at 2.5 to 3.5%.

Here, the self-healing microbial capsule 121 may self-heal ultra-high-performance concrete through calcium carbonate ($CaCO_3$) produced by spore-forming microorganisms capable of self-healing, and the dechlorination microbial capsule 122 may remove chlorine ($Cl^-$) produced by salt damage through an electrical method that allows electrons ($e^-$) emitted from electricity-generating microorganisms to flow through steel fibers incorporated into the ultra-high-performance concrete.

In this case, the self-healing microbial capsules 121 may have a size of 1 μm to 400 μm, and the dechlorination microbial capsules 122 may have a size of 50 μm to 400 μm. Furthermore, the self-healing microorganism may be *Bacillus pasteurii* or *Sporosarcina pasteurii* having the ability to degrade urea, and the electricity-generating microorganism may be *Geobacter*.

Second Example: Marine Concrete (High-Performance Fiber Reinforced Cementitious Composite) Composition Using Dechlorination Microorganisms FIG. 11 is a view illustrating the blending of a high-performance fiber reinforced cementitious composite (HPFRCC) as a marine concrete composition using the dechlorination microorganisms according to a second exemplary embodiment of the present invention.

Referring to FIG. 11, the marine concrete composition using dechlorination microorganisms according to a second example of the present invention is a marine concrete composition formed of a high-performance fiber reinforced cementitious composite (HPFRCC), wherein the high-performance fiber reinforced cementitious composite (HPFRCC) composition includes: 100 parts by weight of cement as a binder (B); as a binder, 10 to 30 parts by weight of silica fume; 100 to 140 parts by weight of fine aggregate; 15 to 30 parts by weight of a filler; 22 to 64 parts by weight of mixing water (W); 1 to 3 parts by weight of an expansion material; 1 to 3 parts by weight of a shrinkage reducing agent; and 10 to 30 parts by weight of a water reducing agent, and for example, the fine aggregate may be quartz sand with a particle diameter of 0.5 mm or less and the filler may be a quartz powder with an average particle diameter of 4 μm, but are not limited thereto. Further, the water reducing agent may be a polycarboxylic acid-based high-performance water reducing agent but is not limited thereto.

In addition, water, which is the mixing water (W), and the binder (B) are mixed such that the ratio (W/B) is 0.2 to 0.4. That is, in the case of the marine concrete composition using dechlorination microorganisms according to the second example of the present invention, water and the binder (B) are mixed such that the ratio (W/B) of water to binder (B) is 0.2 to 0.4 so as to be suitable for a high-performance fiber reinforced cementitious composite (HPFRCC). In the case of the marine concrete composition using dechlorination microorganisms according to the second example of the present invention, the ratio of water to binder (W/B) and the composition of the water reducing agent may be formed to be different from those of the above-described first example.

Furthermore, 1.5 to 3% of steel fiber is incorporated into the cementitious composite based on the total volume of the cementitious composite. That is, the steel fiber as electrically conductive fiber may be incorporated in an amount of 1.5 to 3%, optimally 2 to 2.5% based on the total volume of the cementitious composite.

Further, 0.5 to 2% of self-healing microbial capsules 121 based on the total volume of the cementitious composite and 1 to 5% of dechlorination microbial capsules 122 based on the total volume of the cementitious composite are incorporated, the self-healing microbial capsule 121 may be a carrier of spore-forming microorganisms for self-healing, and the dechlorination microbial capsule 122 may be a carrier of electricity-generating microorganisms for removing chlorine. In this case, the self-healing microbial capsule 121 may be optimally incorporated at 1 to 1.5%, and the dechlorination microbial capsule 122 may be optimally incorporated at 2.5 to 3.5%.

Here, the self-healing microbial capsule 121 may self-heal the cementitious composite through calcium carbonate ($CaCO_3$) produced by spore-forming microorganisms capable of self-healing, and the dechlorination microbial capsule 122 may remove chlorine ($Cl^-$) produced by salt damage through an electrical method that allows electrons ($e^-$) emitted from electricity-generating microorganisms to flow through steel fibers incorporated into the cementitious composite.

In this case, the self-healing microbial capsules 121 may have a size of 1 μm to 400 μm, the dechlorination microbial capsules 122 may have a size of 300 μm to 400 μm, the self-healing microorganism may be *Bacillus pasteurii* or *Sporosarcina pasteurii* having the ability to degrade urea, and the electricity-generating microorganism may also be *Geobacter*.

Ultimately, according to the marine concrete composition using the dechlorination microorganisms according to an exemplary embodiment of the present invention, concrete crack sites may be self-healed through a self-healing microbial capsule carrier, and electrons emitted from electricity-generating microorganisms may be allowed to flow through steel fibers incorporated into ultra-high-performance concrete or high-performance fiber reinforced concrete through a dechlorination microbial capsule carrier to easily remove chlorine generated by seawater through an electrical method.

[Method for Constructing Marine Concrete Structure Using Dechlorination Microorganisms]

FIG. 12 is an operational flow diagram illustrating a method for constructing a marine concrete structure using dechlorination microorganisms according to an exemplary embodiment of the present invention.

Referring to FIG. 12, the method for constructing a marine concrete structure using dechlorination microorganisms according to an exemplary embodiment of the present invention includes first culturing self-healing microorganisms and dechlorination microorganisms, and coating the self-healing microorganisms and the dechlorination microorganisms with a binder to prepare self-healing microbial capsules 121 and dechlorination microbial capsules 122, respectively (S110).

Next, a capsule mixture is formed by mixing a binder (B) consisting of cement and silica fume, a filler and fine aggregate with the self-healing microbial capsules 121 and the dechlorination microbial capsules 122 (S120).

Next, an admixture consisting of an expansion material, a shrinkage reducing agent and a water reducing agent is added to mixing water (W) (S130).

Next, a mortar is formed by mixing the admixture-added mixing water (W) and the capsule mixture so as to have a predetermined water-to-binder ratio (W/B) (S140).

Next, a predetermined amount of steel fiber is incorporated into the mortar based on the total volume of marine concrete to form a marine concrete composition (S150).

Next, the marine concrete composition is formed and cured to construct a marine concrete structure (S160).

Here, the marine concrete composition may be an ultra-high-performance concrete (UHPC) composition or a high-performance fiber reinforced cementitious composite (HP-FRCC) composition with a compressive strength of 120 MPa to 180 MPa.

Specifically, as illustrated in FIG. 10, the ultra-high-performance concrete composition includes: 100 parts by weight of cement as a binder (B); as a binder, 10 to 30 parts by weight of silica fume; 100 to 140 parts by weight of fine aggregate; 15 to 30 parts by weight of a filler; 15 to 25 parts by weight of mixing water (W) based on 100 parts by weight of the cement; 1 to 3 parts by weight of an expansion material; 1 to 3 parts by weight of a shrinkage reducing agent; and 4 to 7 parts by weight of a water reducing agent, and water, which is the mixing water (W), and the binder (B) are mixed such that a ratio (W/B) is 0.2 or less; 1.5 to 3% of steel fiber is incorporated based on the total volume of the ultra-high-performance concrete; and 0.5 to 2% of the self-healing microbial capsule 121 and 1 to 5% of the dechlorination microbial capsule 122 based on the total volume of the ultra-high-performance concrete are incorporated, the self-healing microbial capsule 121 is a carrier of spore-forming microorganisms for self-healing, and the dechlorination microbial capsule may be a carrier of electricity-generating microorganisms for removing chlorine.

In addition, as illustrated in FIG. 11, the high-performance fiber reinforced cementitious composite composition includes: 100 parts by weight of cement as a binder (B); as a binder, 10 to 30 parts by weight of silica fume; 100 to 140 parts by weight of fine aggregate; 15 to 30 parts by weight of a filler; 22 to 64 parts by weight of mixing water (W); 1 to 3 parts by weight of an expansion material; 1 to 3 parts by weight of a water reducing agent; and 10 to 30 parts by weight of a water reducing agent, and water, which is the mixing water (W), and the binder (B) are mixed such that a ratio (W/B) is 0.2 to 0.4; 1.5 to 3% of steel fiber is incorporated based on the total volume of the cementitious composite; and 0.5 to 2% of the self-healing microbial capsule 121 and 1 to 5% of the dechlorination microbial capsule 122 based on the total volume of the cementitious composite are incorporated, the self-healing microbial capsule is a carrier of spore-forming microorganisms for self-healing, and the dechlorination microbial capsule may be a carrier of electricity-generating microorganisms for removing chlorine.

Here, the self-healing microbial capsule 121 may self-heal ultra-high-performance concrete through calcium carbonate ($CaCO_3$) produced by spore-forming microorganisms capable of self-healing, and the dechlorination microbial capsule 122 may remove chlorine ($Cl^-$) produced by salt damage through an electrical method that allows electrons ($e^-$) emitted from electricity-generating microorganisms to flow through steel fibers incorporated into the ultra-high-performance concrete, and in this case, the self-healing microorganism may be *Bacillus pasteurii* or *Sporosarcina pasteurii* having the ability to degrade urea, and the electricity-generating microorganism may be *Geobacter.*

Ultimately, according to an exemplary embodiment of the present invention, the problem of reduced durability against salt damage of ultra-high-performance concrete or high-performance fiber reinforced concrete for application to marine construction environments can be fundamentally prevented through a dechlorination microbial capsule carrier.

The above-described description of the present invention is provided for illustrative purposes, and a person skilled in the art to which the present invention pertains will understand that the present invention can be easily modified into other specific forms without changing the technical spirit or essential features of the present invention. Therefore, it should be understood that the above-described examples are only illustrative in all aspects and not restrictive. For example, each constituent element which is described as a singular form may be implemented in a distributed form, and similarly, constituent elements which are described as being distributed may be implemented in a combined form.

The scope of the present invention is represented by the claims to be described below rather than the detailed description, and it should be interpreted that the meaning and scope of the claims and all the changes or modified forms derived from the equivalent concepts thereto fall within the scope of the present invention.

REFERENCE NUMBERS LIST

110: Marine concrete (UHPC or HPFRCC)
121: First microbial capsule
122: Second microbial capsule
131: Metabolite
132: Nutrient
141: Spore-forming microorganism
142: Electricity-generating microorganism

The invention claimed is:

1. A marine concrete composition formed of ultra-high-performance concrete (UHPC), wherein the ultra-high-performance concrete (UHPC) composition comprises:

100 parts by weight of cement as a binder (B); as a binder, 10 to 30 parts by weight of silica fume; 100 to 140 parts by weight of fine aggregate; 15 to 30 parts by weight of a filler; 15 to 25 parts by weight of mixing water (W) based on 100 parts by weight of the cement; 1 to 3 parts by weight of an expansion material; 1 to 3 parts by weight of a shrinkage reducing agent; and 4 to 7 parts by weight of a water reducing agent, and water, which is the mixing water (W), and the binder (B) are mixed such that a ratio (W/B) is 0.2 or less;

1.5 to 3% of steel fiber is incorporated based on the total volume of the ultra-high-performance concrete; and 0.5 to 2% of self-healing microbial capsules and 1 to 5% of dechlorination microbial capsules based on the total volume of the ultra-high-performance concrete are incorporated, the self-healing microbial capsule is a carrier of spore-forming microorganisms for self-healing, and the dechlorination microbial capsule is a carrier of electricity-generating microorganisms for removing chlorine.

2. The marine concrete composition of claim 1, wherein the self-healing microbial capsule self-heals the ultra-high-performance concrete through calcium carbonate ($CaCO_3$) produced by the spore-forming microorganisms capable of self-healing, and the dechlorination microbial capsule removes chlorine ($Cl^-$) produced by salt damage through an electrical method that allows electrons ($e^-$) emitted from the electricity-generating microorganisms to flow through steel fibers incorporated into the ultra-high-performance concrete.

3. The marine concrete composition of claim 1, wherein the self-healing microbial capsules have a size of 1 μm to 400 μm, and the dechlorination microbial capsules have a size of 50 μm to 400 μm.

4. The marine concrete composition of claim 1, wherein the self-healing microorganism is *Bacillus pasteurii* or *Sporosarcina pasteurii* having the ability to degrade urea.

5. The marine concrete composition of claim 3, wherein the electricity-generating microorganism is *Geobacter*.

6. A marine concrete composition formed of a high-performance fiber reinforced cementitious composite (HP-FRCC), wherein the high-performance fiber reinforced cementitious composite (HPFRCC) composition comprises:

100 parts by weight of cement as a binder (B); as a binder, 10 to 30 parts by weight of silica fume; 100 to 140 parts by weight of fine aggregate; 15 to 30 parts by weight of a filler; 22 to 64 parts by weight of mixing water (W); 1 to 3 parts by weight of an expansion material; 1 to 3 parts by weight of a shrinkage reducing agent; and 10 to 30 parts by weight of a water reducing agent, and water, which is the mixing water (W), and the binder (B) are mixed such that a ratio (W/B) is 0.2 to 0.4;

1.5 to 3% of steel fiber is incorporated based on the total volume of the cementitious composite; and 0.5 to 2% of self-healing microbial capsules and 1 to 5% of dechlorination microbial capsules based on the total volume of the cementitious composite are incorporated, the self-healing microbial capsule is a carrier of spore-forming microorganisms for self-healing, and the dechlorination microbial capsule is a carrier of electricity-generating microorganisms for removing chlorine.

7. The marine concrete composition of claim 6, wherein the self-healing microbial capsule self-heals the cementitious composite through calcium carbonate ($CaCO_3$) produced by the spore-forming microorganisms capable of self-healing, and the dechlorination microbial capsule removes chlorine ($Cl^-$) produced by salt damage through an electrical method that allows electrons ($e^-$) emitted from the electricity-generating microorganisms to flow through steel fibers incorporated into the cementitious composite.

8. The marine concrete composition of claim 6, wherein the self-healing microbial capsules have a size of 1 μm to 400 μm, and the dechlorination microbial capsules have a size of 300 μm to 400 μm.

9. The marine concrete composition of claim 6, wherein the self-healing microorganism is *Bacillus pasteurii* or *Sporosarcina pasteurii* having the ability to degrade urea.

10. The marine concrete composition of claim 6, wherein the electricity-generating microorganism is *Geobacter*.

* * * * *